(12) United States Patent
King et al.

(10) Patent No.: US 7,501,270 B2
(45) Date of Patent: Mar. 10, 2009

(54) OXYGEN-RESISTANT HYDROGENASES AND METHODS FOR DESIGNING AND MAKING SAME

(75) Inventors: Paul King, Golden, CO (US); Maria L Ghirardi, Lakewood, CO (US); Michael Seibert, Lakewood, CO (US)

(73) Assignee: Allaince for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 10/553,097

(22) PCT Filed: Apr. 16, 2004

(86) PCT No.: PCT/US2004/011830

§ 371 (c)(1),
(2), (4) Date: Oct. 13, 2005

(87) PCT Pub. No.: WO2004/093524

PCT Pub. Date: Nov. 4, 2004

(65) Prior Publication Data

US 2006/0228774 A1    Oct. 12, 2006

Related U.S. Application Data

(60) Provisional application No. 60/464,081, filed on Apr. 18, 2003.

(51) Int. Cl.
*C12N 9/02* (2006.01)
*C12N 1/12* (2006.01)
*C12N 15/74* (2006.01)
*C12Q 1/68* (2006.01)
*C12P 21/06* (2006.01)
*C12P 3/00* (2006.01)
*C07H 21/04* (2006.01)

(52) U.S. Cl. .......................... 435/189; 435/6; 435/69.1; 435/168; 435/257.2; 435/471; 536/23.2

(58) Field of Classification Search ................ 435/189, 435/6, 69.1, 168, 257.2, 471; 536/23.2
See application file for complete search history.

(56) References Cited

U.S. PATENT DOCUMENTS

| | | |
|---|---|---|
| 4,532,210 A | 7/1985 | Miura et al. |
| 5,100,781 A | 3/1992 | Greenbaum |
| 5,270,175 A | 12/1993 | Moll |
| 5,426,040 A | 6/1995 | Cheney et al. |
| 5,661,017 A | 8/1997 | Dunahay et al. |
| 5,691,190 A | 11/1997 | Girard et al. |
| 5,871,952 A | 2/1999 | Ghirardi et al. |
| 6,448,068 B2 | 9/2002 | Seibert et al. |
| 2001/0053543 A1 | 12/2001 | Melis et al. |
| 2002/0034817 A1 | 3/2002 | Henry et al. |
| 2004/0209256 A1* | 10/2004 | Dillon .......................... 435/6 |

OTHER PUBLICATIONS

Forestier et al. GenBank Acession No. AY055755, "Chlamydomonas reinhardtii iron-hydrogenase HydA mRNA", created Dec. 31, 2001.*

* cited by examiner

*Primary Examiner*—Rebecca E Prouty
*Assistant Examiner*—Iqbal H Chowdhury
(74) *Attorney, Agent, or Firm*—Paul J. White; John C. Stolpa; Mark D. Trenner

(57) ABSTRACT

The invention provides oxygen- resistant iron-hydrogenases ([Fe]-hydrogenases) for use in the production of H2. Methods used in the design and engineering of the oxygen-resistant [Fe]-hydrogenases are disclosed, as are the methods of transforming and culturing appropriate host cells with the oxygen-resistant [Fe]-hydrogenases. Finally, the invention provides methods for utilizing the transformed, oxygen insensitive, host cells in the bulk production of $H_2$ in a light catalyzed reaction having water as the reactant.

7 Claims, 6 Drawing Sheets

```
CaI      PVAALKEKS-HIEKVQEALND-PKKHVIVAMAPSVRTAMGELPKMGYCKD  247
CpI      PVAALSEKS-HMDRVKNALNA-PEKHVIVAMAPSVRASIGELPNMGFCVD  248
Dd       PENALYEAQSWVPEVERKLKD-GRVKCIAMPAPAVRYALGDAFGMPVCSV   98
CrHydA2  ATDAVPHWKLALEELDKPKDG-GRKVEIAQVAPAVRVAIAESFGLAPCAV  113
CrHydA1  AEAPISHVQQAIAEIAKPKDDPTKKHMCVQVAPAVRVAIAETLGLAPCAT  110

CaI      VTKLIYTAEMGELEKVEIINEGLMTDEISEAEEIGEK--------NN  289
CpI      VTGKIYTALEQLGFEKSEIINEGLMTDEISEAEELQKIE--------NN  290
Dd       TTGKMLAALQKLGFAHCWDTEFTADVTIWEEGSEFVERLTK------KSD  142
CrHydA2  SPGKIATGIRAGEFEQIEITLEAIELENESEGILEHELKEHLEAHPHSD  163
CrHydA1  TPKQLAEGLRRLGFDEVFDTLPGADLTIMPEGSELIHRETEHLEAHPHSD  160

CaI      GPEPMETSCCPAWIRLIQNYHPELIDNESSAKSPQLIFGTASKTIYPSIS  339
CpI      GPEPMETSCCPGWVRQIENYFPELINNESSAKSPQIIFGTASKTIYPSIS  340
Dd       MPIPQPTSCCPGWQKYAETYFPELLPHESTCKSPIGMNGALAKTYGAERM  192
CrHydA2  EPLPMFTSCCPGWVAMMEKSYPELIPFVSSCKSPQMMMGAMVKTYLSEKQ  213
CrHydA1  EPLPMFTSCCPGWIAMEEKSYPDLIPYVSSCKSPQMMLAAMVKSYLAEKK  210

CaI      GIAPEDVYTVTLMPCNDKKYEADIPFMETNS---LRDIDASITTRELAKM  386
CpI      GDPEKNVFTVTVMPCTSKKFEADRPQMEKDG---LRDIDAVITTRELAKM  387
Dd       KYDPKQVYTVSIMPCIAKKYEGLRPELKSSG---MRDIDATITTRELAYM  239
CrHydA2  GIPAKDIVMVSVMPCVRKQGEADREWFCVSE-PGVRDVDHVITTAELGNI  262
CrHydA1  GIAPKDMVMVSIMPCTRKQSEADRDWFCVDADPTLRQLDHVITTVELGNI  260

CaI      IKDAKIKEADLEDGEVDPAMCTYSGAGAIFGATGGVMEAAIRSAKDEAEN  436
CpI      IKDAKIPEAKLEDSEADPAMCEYSGAGAIFGATGGVMEAALRSAKDEAEN  437
Dd       IKKAGIDEAKLPDGKRDSLMGESTGGATIFCVTGGVMEAALRFAYEAVTG  289
CrHydA2  RKERGINLPELPDSIWDQPLGLGSGAGVIFGTTGGVMEAALRTAYEIVTK  312
CrHydA1  RKERGINLAELPEGEWDNPMGVGSGAGVIFGTTGGVMEAALRTAYELFTG  310

CaI      KELENVDYTEVRGEKGIKEAEVETA-------------------------  461
CpI      AELEDIEYKQVRGENGIKEAEVETN-------------------------  462
Dd       KKPDSWDFKAVRGEDGIKEATVNVG-------------------------  314
CrHydA2  EPLPRLNLSEVRGEDGIKEASVTIVPAPGSKFAELVAERLAHKVEEAAAA  362
CrHydA1  TPLPRLSLSEVRGMDGIKETNITMVPAPGSKFEELLKHRAAARAEAAAHG  360

CaI      ------------------------------GNKLNVAVINGASNEPEMKS  482
CpI      ------------------------------NNKYNVAVINGASNIFKEMKS  483
Dd       ------------------------------GTDVKVAVVHGAKREKQVCDD  335
CrHydA2  EAAAAVEGAVKPPIAYDGGQGFSTDDGKGCLKLRVAVANGEGNAKKLIGK  412
CrHydA1  TPG---------PLAWDGGAGFTSEDGRGCITLRVAVANGEGNAKKLITK  401

CaI      GKMNEKQYHFIEVMACEGGCINGGGQPHVNALDRENVDYRKLRASVLYNQ  532
CpI      GMINEKQYHFIEVMACHGGCVNGGGQPHVNPKDLEKVDIKKVRASVLYNQ  533
Dd       VKAGKSPYHFIEYMACEGGCVCGGGQPVMPGVLEA---------------  370
CrHydA2  MVSGEAKYDFVEIMACEAGCVGGGGQPRSTDKQITQK-----RQAALYDL  457
CrHydA1  MQAGEAKYDFVEIMACEAGCVGGGGQPRSTDKAITQK-----RQAALYNL  446
```

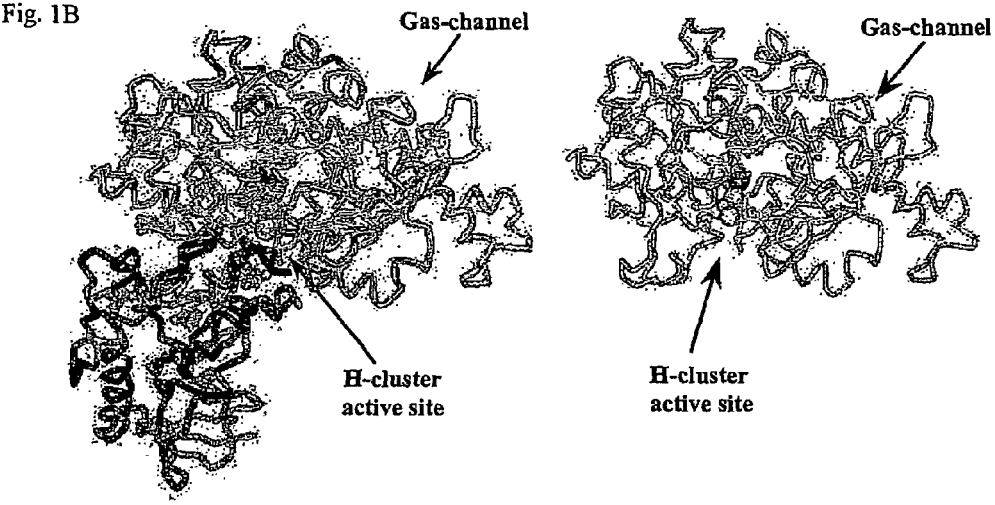

Fig. 2

```
Cr HydA1    AAPAAEAPLSHVQQALAELAKPKDDPTRKHVCVQVAPAVRVAIAETLGLAPGATTPKQLA  60
CpI          CIIACPVAALSEKSHMDRVKNALNAPEKHVIVAMAPSVRASIGELFNMGFGVDVTGKIY  59

Cr HydA1    EGLRRLGFDEVFDTLFGADLDIMEEGSELLHRITEDEPLPMFTSCCPGWIAMLEKSYPDL  120
CpI          TALRQLGFDKIFDINFGADMTIMEEAIELVQRIENNGPFPMFTSCCPGWVRQAENYYPEL  119

Cr HydA1    IPYVSSCKSPQMMLAAMVKSYLAEKKGIAPKDMVMVSIMPCTRKQSEADRDWFCVDADPT  180
CpI          LNNLSSAKSPQQIFGTASKTYYPSISGLDPKNVFTVTVMPCTSKKFEADRPQMEKDG---  176

Cr HydA1    LRQLDHVITTVELGNIFKERGINLAELPEGEWDNPMGVGSGAGVLFGTTGGVMEAALRIA  240
CpI          LRDIDAVITTRELAKMIKDAKIPFAKLEDSEADPAMGEYSGAGAIFGATGGVMEAALRSA  236

Cr HydA1    YELFTGTPLPRLSLSEVRGMDGIKETNITMVPATLRVAVANGLGNAKKLITKMQAGEAKY  300
CpI          KDLFENAELEDIEYKQVRGLNGIKEAEVEINNNKYNVAVINGASNLFKFMKSGMINEKQY  296

Cr HydA1    DEVELMACPAGCVGGGGQPRSTDKAITQKRQAALYNLDEKSTLRRSHENPSIRELYDTYL  360
CpI          HEPELMACHGGCVNGGGQPHVNPKDIKKVRASVLYNQDEHLSKRKSHENTALVKMYQNYF  356

Cr HydA1    GEPLGHKAHELLHTHYVAGGVEEKDEKK  388
CpI          GKPGEGRAHEILHFKYKK----------  374
```

Fig. 3
A.
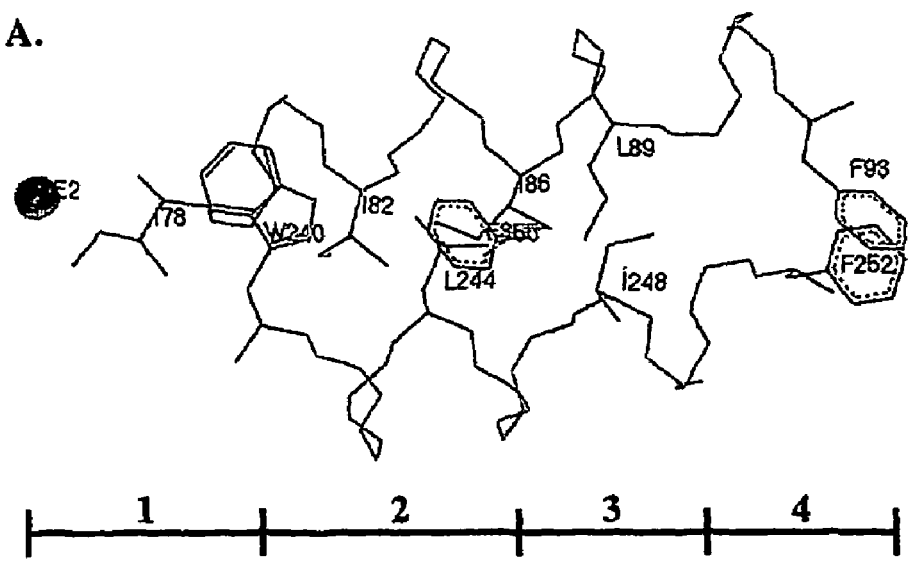
B.
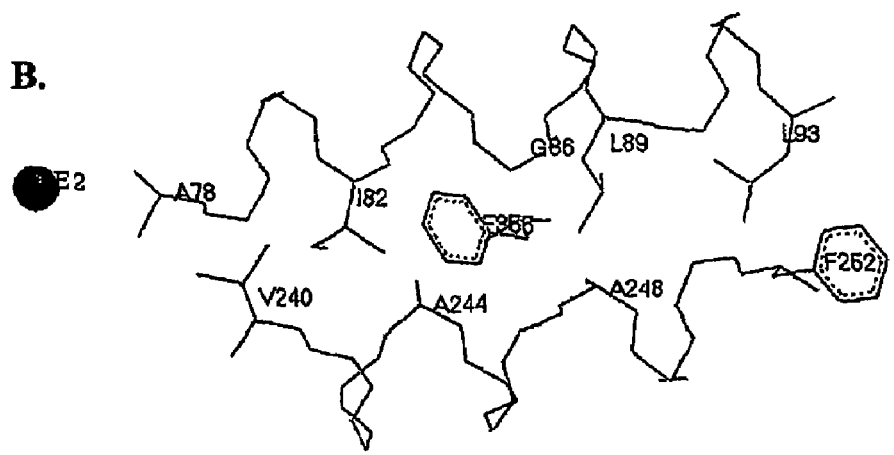

Fig. 6          H₂ Electrode Assay
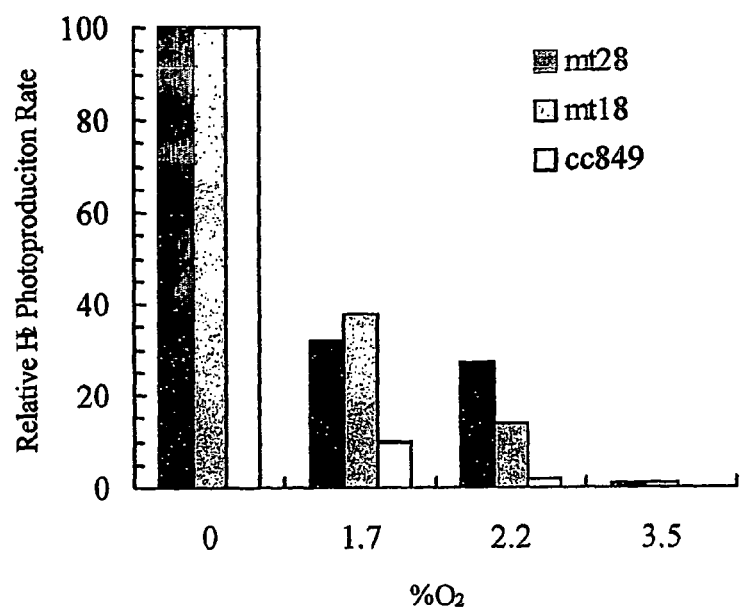
Fig. 7          MV Assay
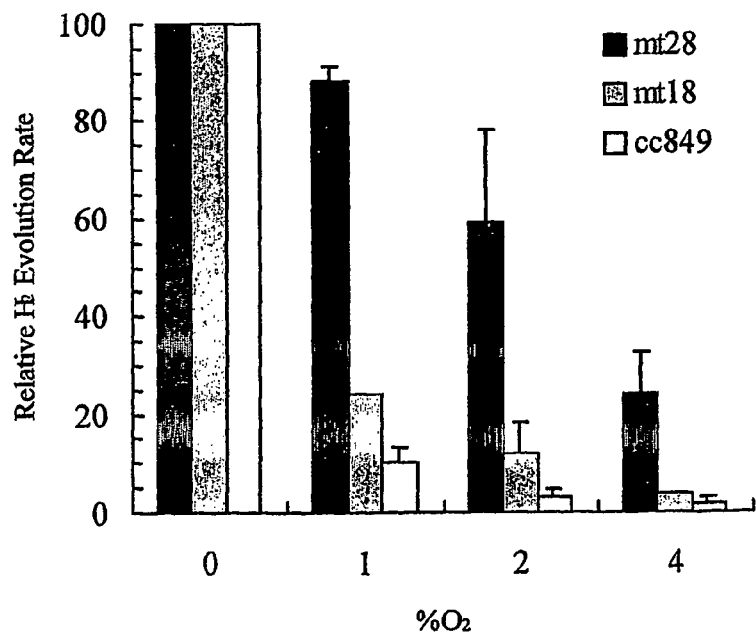

OXYGEN-RESISTANT HYDROGENASES AND METHODS FOR DESIGNING AND MAKING SAME

This application is a 371 US filing of PCT/US04/11830 filed on Apr. 16, 2004, which claims benefit of US provisional application 60/464,081 filed on Apr. 18, 2003.

GOVERNMENT INTEREST

The United States Government has rights in this invention pursuant to contract DE-AC36-99GO10337 between the United States Department of Energy and the National Renewable Energy Laboratory, a division of Midwest Research Institute.

FIELD OF THE INVENTION

The present invention relates to hydrogen-production by microorganisms, for example hydrogen production by green algae. More specifically, the invention relates to methods for designing and engineering hydrogenase enzymes with improved oxygen resistance, and to the methods for transforming microorganisms to express these oxygen-resistant hydrogenase enzymes for use in the production of hydrogen in an oxygen containing environment.

BACKGROUND OF THE INVENTION

Hydrogen ($H_2$) is becoming an attractive alternative energy source to fossil fuels due to its clean emissions and potential for cost effective production by microorganisms. As such, microorganisms that metabolize $H_2$ are being investigated for their potential use in $H_2$-production. A microorganism of particular interest for $H_2$ production is the green alga, *Chlaydomonas reinhardtii*, which is able to catalyze light-dependent, $H_2$ production utilizing water as a reductant. Ghiradi et al., (2000) Trends Biotech. 18(12):506-511; Melis et al., (2001) Plant Physiol. 127:740-748. The benefits of using an algal system for $H_2$-production include the use of renewable substrates (light and water) and its potential cost-effectiveness. Melis A, Int. J. Hyd. Energy 27:1217-1228. As such, there is a great deal of interest in optimizing $H_2$-production by green algae to maximize the potential benefit as an alternative energy source.

*Chlamydomonas reinhardtii*, and other like microorganisms, are able to express a class of $H_2$ metabolizing enzymes called hydogenases. Members of this enzyme family function in either $H_2$-uptake (as a means to provide reductant for substrate oxidation) or $H_2$-production (as a means to eliminate excess reducing equivalents). Characterization of various hydrogenases from multiple organisms has identified three principle hydrogenase types, broadly classified by the chemical nature of their active sites: [Fe]-hydrogenase, [NiFe]-hydrogenase, and non-metallic (organic) hydrogenase. Vignais et al, (2001) FEMS Micro. Rev. 25:455-501; Adams M. W., Biochem. Biophys. Acta. 1020:115-145; Buurman et al., (2000) FEBS Letts. 485:200-204. More particularly, [Fe]-hyrdogenase have an active site containing a [4Fe-4S]-center bridged to a [2Fe-2S]-center (H-cluster) (Peters et al., (1998) Science 282:1853-1858; Nicolet et al., (1998) Structure 7:13-23), and the [NiFe]-hydrogenase have an active site containing a [4Fe4S]-center bridged to a [NiFe]-center (Volbeda et al., (1995) Nature 373:580-587). Coordination of the metal prosthetic groups to the active sites is made by cysteinyl, $CN^-$, and $CO$ ligands. Further, within each hydrogenase group are monomeric, or multimeric enzymes, that can be either cytoplasmic or membrane bound within the cell. Vignais et al., Supra.

Although there are differences within the active sites between different families of hydrogenase, as well as between the subunit composition and localization between hydrogenase families, most, if not all studied hydrogenases have exhibited some degree of sensitivity to inhibition by CO and $O_2$. Adams M. W. W; Volbeda et al., (1990) Int. J. Hyd. Energy 27:1449-1461. Hydrogenase sensitivity to these inhibitors correlates to some degree to the type of prosthetic group that forms the active site, for example, [Fe]-hydrogenase is highly sensitive to $O_2$. As such, for example, the activity of [Fe]-hydrogenase in *C. reinhardtii* is very sensitive to $O_2$ during $H_2$-photoproduction under photosynthetic conditions. Ghirardi et al., (1997) App. Biochem. Biotech. 63-65: 141-151. Oxygen inhibition of [Fe]-hydrogenases is a major drawback in the use of green alga for $H_2$ production.

One approach to overcoming this $H_2$ production limitation is to stress the *C. reinhardtii* under photoheterotrophic, sulfur-deprived conditions that minimize $O_2$-photoproduction levels and result in sustained $H_2$-production. However, this approach does not result in optimal yields and requires the use of suilir-deprived/oxygen limited production techniques. Recently, CO and $O_2$ inhibition of hydrogenase activity in alga has been focused on the putative role of the $H_2$-channel. For example, it has been shown that the positioning of the $Fe_2$-atom in the enzyme's active site is directly at the active-site/$H_2$-channel interphase, where it is easily accessed by either CO or $O_2$ diffusing through the channel. Lemon et al., (1999) Biochem. 38:12969-12973; Bennett et al., (2000) Biochem. 39:7455-7460. Further, a naturally occurring $O_2$-resistant [NiFe]-hydrogenase has been shown to have a narrower active site/$H_2$-channel interphase than the naturally occurring hydrogenase counterpart. Volbeda et al. (2002), Supra.

Against this backdrop the present invention has been developed.

SUMMARY OF THE INVENTION

The present invention provides oxygen-resistant hydrogenases for use in the bulk production of $H_2$ in green algae cultures. In a preferred embodiment, homology modeling between known hydrogenases, eg., CpI, and target hydrogenases, e.g., HydA1, was used to design and in silico engineer an oxygen-resistant [Fe]-hydrogenase having a reduced diameter $H_2$-channel. Constructed polynucleotides that encode oxygen-resistant [Fe]-hydrogenase enzymes are used to transform target host cells which were subsequently used in the photoproduction of $H_2$. In preferred embodiments, the target host cells are *C. reinhardtii*. The invention provides a solution to the problem of $H_2$ production by green algae when $O_2$ is present in the environment.

The present invention also provides host cells expressing oxygen-resistant [Fe]-hydrogenase. Host cells expressing the oxygen-resistant [Fe]-hydrogenase have significantly increased $H_2$ production, in the presence of $O_2$, as compared to similarly treated cells that do not express oxygen-tolerant [Fe]-hydrogenase.

The present invention also provides polynucleotide molecules encoding HydA1V240W and other like oxygen-resistant hydrogenase polypeptides. The invention includes nucleic acid molecules that hybridize under high stringency conditions to the HydA1V240W polynucleotides (and other like oxygen-resistant hydrogenase polynucleotides) of the present invention. The invention also includes variants and derivatives of the oxygen-resistant [Fe]-hydrogeanse polypeptides, including fusion proteins that confer a desired function. The invention also provides vectors, plasmids, expression systems, host cells and the like, containing the oxygen-resistant [Fe]-hydrogenase of the invention.

These and various other features and advantages of the invention will be apparent from a reading of the following detailed description and a review of the appended claims.

BRIEF DESCRIPTION OF THE DRAWINGS

FIG. 1A shows a protein alignment using PILEUP/GENE-DOC program (CaI is represented by SEQ ID NO: 1; CpI is represented by SEQ ID NO: 2; Dd is represented by SEQ ID NO: 3; CrHydA2 is represented by SEQ ID NO: 4; CrHydA1 is represented by SEQ ID NO: 5). Amino acid residues highlighted in black represent identities between at least 5 of the iron- hydrogenases, and those highlighted in grey show similarity between at least 5 of the sequences (1A). FIG. 1B shows a theoretical structure of HydA1 using homology modeling to the solved X-ray structure of CpI. The left panel shows an overlay of HydA1 and CpI, with locations of the $H_2$-channels and the active sites, while the right panel shows the HydA1 structure.

FIG. 2 shows the protein sequence of HydA1 (SEQ ID NO: 6) aligned to the catalytic core region of CpI (SEQ ID NO: 7). The sequences that form the $H_2$-channel domain are shaded either gray (similar) or black (identical).

FIGS. 3A and 3B show how mutations made to the HydA1 $H_2$-channel result in predicted $H_2$-channel structures. Wild type HydA1 H2-channel structure is shown in 3B, while mutant H2-channel structures are shown in 3A. Note that for reference purposes, the channel has been divided into four zones (black line numbered 1-4).

FIG. 6 illustrates hydrogenase activity as measured by the rate of H2 evolved ($\mu$mol $H_2$/mg ch$1^{-1}$/h$^{-1}$) under variant $O_2$ concentrations (0 to 3.5% final $O_2$ concentration) and plotted relative to the activity value obtained under completely anaerobic conditions.

FIG. 7 shows the activity of $O_2$-resistant [Fe]-hydrogenase as measured in a reduced MV assay. Samples of induced cells were taken and assayed for hydrogenase activity following exposure to various levels of $O_2$ (0-4% final $O_2$ concentration). Note that hydrogenase activity was measured as the rate of H2 evolved ($\mu$mol $H_2$/mg chl$^{-1}$/h$^{-1}$) over a 30-minute incubation period and plotted relative to the activity value obtained under completely anaerobic conditions.

DETAILED DESCRIPTION OF THE INVENTION

Definitions

Figure 4:
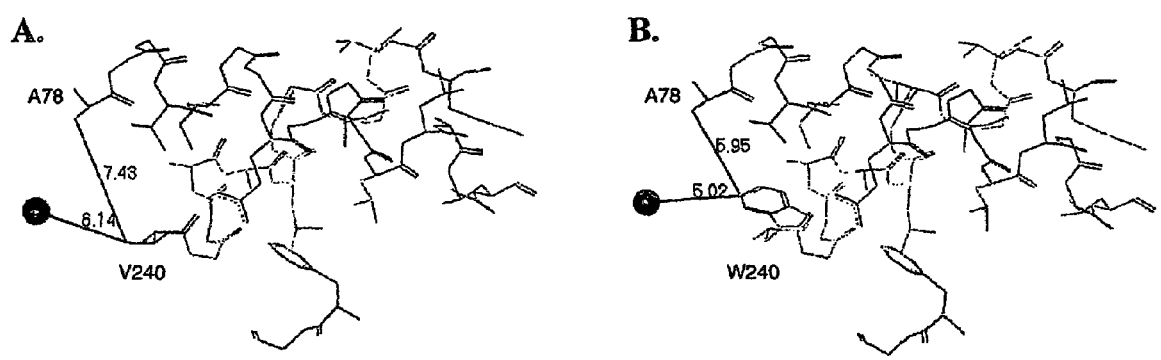
FIGS. 4A and 4B show side-orientation views from the active site (left) to the protein surface (right) of the $H_2$-channel of the wild type HydA1 (4A) and mutant HydA1V240W (4B).

The following definitions are provided to facilitate understanding of certain terms used herein and are not meant to limit the scope of the present disclosure.

"Amino acid" or "residues" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross-linking, iodination, methylation, and alike. Amino acid residue characterization can be found in numerous citations, for example Stryer, 1995, Biochemistry, throughout the text and 17-44.

"Expression" refers to transcription and translation occurring within a host cell. The level of expression of a DNA molecule in a host cell may be determined on the basis of either the amount or corresponding mRNA that is present within the cell or the amount of DNA molecule encoded protein produced by the host cell (Sambrook et al., 1989, Molecular Cloning: A Laboratory Manual, 18.1-18.88).

"Genetically engineered" refers to any recombinant DNA or RNA method used to create a host cell that expresses a target protein at elevated levels, at lowered levels, or in a mutated form. Typically, the host cell has been transfected, transformed, or transduced with a recombinant polynucleotide molecule, and thereby been altered so as to cause the cell to alter expression of the desired protein. Methods for genetically engineering host cells are well known in the art. (See Current Protocols in Molecular Biology, Ausubel et al., eds. (Wiley & Sons, New York, 1988, and quarterly updates)). Genetically engineering techniques include but are not limited to expression vectors, targeted homologous recombination and gene activation (see, for example U.S. Pat. No. 5,272,071 to Chappel) and trans activation by engineered transcription factors (See Segal et al., 1999, Proc Natl Acad Sci USA 96(6):2758-63).

"Hybridization" refers to the pairing of complementary polynucleotides during an annealing process. The strength of hybridization between two polynucleotide molecules is impacted by the homology between the two molecules, stringency of the conditions involved, and melting temperatures of the formed hybrid and the G:C ratio within the polynucleotide. For purposes of the present invention stringency hybridization conditions refers to the temperature, ionic strength, solvents, etc, under which hybridization between polynucleotides occurs.

"Identity" refers to a comparison between pairs of nucleic acid or amino acid molecules. Methods for determining sequence identity are known in the art. For example, computer programs have been developed to perform the comparison, such as the Gap program (Wisconsin Sequence Analysis Package, Version 8 for Unix, Genetics Computer Group, University Research Park, Madison Wis.), that uses the algorithm of Smith and Waterman (1981) Adv Appl Math 2:482-489.

"Isolating" refers to a process for separating a nucleic acid or polypeptides from at least one contaminant with which it is normally associated. In preferred embodiments, isolating refers to separating a nucleic acid or polypeptide from at least 50% of the contaminants with which it is normally associated, and more preferably from at least 75% of the contaminants with which it is normally associated.

The term "nucleic acid" refers to a linear sequence of nucleotides. The nucleotides are either a linear sequence of polyribonucleotides or polydeoxyribonucleotides, or a mixture of both. Examples of nucleic acid in the context of the present invention include—single and double stranded DNA, single and double stranded RNA, and hybrid molecules that have mixtures of single and double stranded DNA and RNA. Further, the nucleic acids of the present invention may have one or more modified C) nucleotides.

The term "PCR" or "polymerase chain reaction" refers to the process to amplify nucleic acids as described in U.S. Pat. Nos. 4,683,105 and 4,683,202, both owned by Roche Molecular.

"Host cell" refers to cells containing a target nucleic acid molecule, for example a heterologous nucleic acid molecule such as a plasmid or other low molecular weight nucleic acid, in which case the host cell is typically suitable for replicating the nucleic acid molecule of interest. Examples of suitable host cells useful in the present invention include bacteria, algae, and yeast. Specific examples of such cells include *E. Coli* DH5α cells, as well as various other bacterial cell sources, for example, the *E. Coli* strains: DH10b cells, XL1Blue cells, XL2Blue cells, Top10 cells, BB101 cells, and DH12S cells, yeast host cells from the genera including *Saccharomyces, Pichia*, and *Kluveromyces*, and green alga, for example, *Chlamydomonas reinhardtii*.

"Hybridization" refers to the pairing of complementary polynucleotides during an annealing period. The strength of hybridization between two polynucleotides molecules is impacted by the homology between the two molecules, stringent conditions involved, the melting temperature of the formed hybrid and the G:C ratio within the polynucleotides. High stringency conditions include, for example, 42° C., 6×SSC, 0.1% SDS for 2 hours.

"Nucleic acid" or "NA" refers to both a deoxyribonucleic acid and a ribonucleic acid. As used herein, "nucleic acid sequence" refers to the order or sequence of deoxyribonucleotides or ribonucleotides along a strand. They may be natural or artificial sequences, and in particular genomic DNA (gDNA), complementary DNA (cDNA), messenger RNA (mRNA), transfer RNA (tRNA), ribosomal RNA (rRNA), hybrid sequences or synthetic or semisynthetic sequences, oligonucleotides which are modified or otherwise. These nucleic acids may be of human, animal, plant, bacterial or viral origin and the like. They may be obtained by any technique known to persons skilled in the art, and in particular by the screening of libraries, by chemical synthesis or by mixed methods including the chemical or enzymatic modification of sequences obtained by the screening of libraries. They may be chemically modified, e.g. they may be pseudonucleic acids (PNA), oligonucleotides modified by various chemical bonds (for example phosphorothioate or methyl phosphonate), or alternatively oligonucleotides which are functionalized, e.g. which are coupled with one or more molecules having distinct characteristic properties. In the case of deoxyribonucleic acids, they may be single- or double-stranded, as well as short oligonucleotides or longer sequences. In particular, the nucleic acids advantageously consist of plasmids, vectors, episomes, expression cassettes and the like. These deoxyribonucleic acids may carry genes of therapeutic interest, sequences for regulating transcription or replication, antisense sequences which are modified or otherwise, regions for binding to other cellular components, and the like.

"Oxygen resistant" refers to any measurable decrease in oxygen sensitivity in a hydrogenase as compared to a hydrogenase having a reference oxygen sensitivity, for example, as compared to a wild type hydrogenase from which an oxygen-resistant hydrogenase enzyme has been made.

"Oxygen sensitive" refers to the wild type or reference oxygen sensitivity found in a native hydrogenase.

"Protein," "peptide," and "polypeptide" are used interchangeably to denote an amino acid polymer or a set of two or more interacting or bound amino acid polymers.

Green Algae and Iron Hydrogenase

Green algae, e.g., *Chlamydomonas reinhardtii*, cultured under anaerobic conditions synthesize an enzyme known as iron-hydrogenase ([Fe]-hydrogenase). As shown in FIG. 1A, several representative [Fe]-hydrogenase enzymes are aligned showing general sequence identity for the family of proteins. Generally, overall sequence identity for [Fe]-hydrogenase family members is usually at least 45% and sequence identity for the $H_2$-channel between family members is at least 66%.

In general, [Fe]-hydrogenase enzymes characteristically possess a catalytic site consisting of a bimetallic center containing two Fe atoms (2Fe-center), bridged by cysteinyl sulfur to an electron relay [4Fe4S] center (4Fe-center). The iron atoms of the catalytic 2Fe-center are joined together by a combination of organic, sulfur, and carbon monoxide ligands. The chemistry of the [Fe]-hydrogenase catalytic core is reactive with respect to hydrogen, typically possessing very high hydrogen-production rates. However, this same catalytic core is also highly sensitive to inactivation by oxygen. As a protective measure against inactivation by oxygen or other like molecules, the catalytic core is typically buried deep within the protein, where access to the core is limited. As a result, interface of the hydrogenase catalytic site with surface surroundings is principally limited to a single channel, termed the $H_2$-channel, that directs diffusion of synthesized hydrogen from the enzyme interior to the external environment. The $H_2$-channel is also the primary access route of oxygen to the metallo-catalytic site within hydrogenase enzyme. Reverse diffusion of the oxygen from the surface of the enzyme into the $H_2$-channel and on to the active site, allows oxygen to bind to the 2Fe-center, inactivating the enzyme. Under normal physiologic conditions this represents a fairly normal inhibitory response for the hydrogenase enzyme, however, under the artificial conditions of expressing bulk amounts of $H_2$, this is a fairly major limitation.

The present invention provides for the modification of the $H_2$-channel to reduce oxygen diffusion from the external environment to the enzyme's catalytic core. The present invention provides modifications to the $H_2$-channel that act as oxygen filters, preventing or reducing the diffusion of oxygen to the catalytic site within the hydrogenase enzyme. These modifications are at the same time insufficient to limit the ability of $H_2$ to diffuse out of the enzyme through the $H_2$-channel. Several mechanisms for the reduction of oxygen diffusion to the active site within the hydrogenase enzyme are provided, including targeted replacement of residues that line the $H_2$-channel with bulkier residues, so as to shield the 2Fe-center and/or reduce the diameter of the $H_2$-channel. In particular, the residues that line the $H_2$-channel are replaced with bulkier, hydrophobic residues, for example tryptophan or phenylalanine, so as to shield the 2Fe-center, as well as to reduce the size or volume of the catalytic site-$H_2$-channel interface. In addition, modifications to residues on the channel interior that approach and define the channel-solvent boundary (see portion 4 of FIG. 3).

In a preferred embodiment of the invention, a process for designing and engineering oxygen-resistant iron-hydrogenases has been developed. The engineering scheme targets the structure and or environment of the H$_2$-channel within the target hydrogenase, which is altered to be more selective in allowing the outward diffusion of hydrogen while simultaneously filtering out surface oxygen. Note that size-limited diffusion has been successfilly used to generate filters for commercial use in the separation of gases, including the separation of hydrogen from oxygen. Menoff T. M., (2000) Proc. Hydrogen Program Review.

The present invention provides host cells for the expression of nucleic acid molecules for encoding an oxygen-resistant iron-hydrogenase, for example, *C. reinhardtii* that expresses an oxygen-resistant HydA1 or cyanobacteria that also expresses an oxygen-resistant HydA1. Example oxygen-resistant hydrogenases designed and engineered by the method of the present invention include V240W, A78W, A244W, A248W, G86W, and L93W. These oxygen-resistant hydrogenase enzymes have the same primary structure as HydA1 with the exception that A at residue 78 is replaced with W. Note that other residues besides W, including synthetic and derivatized amino acids, are envisioned for substitution into the H$_2$-channel, as long as they limit O$_2$ diffusion through the channel and allow H$_2$ diffusion out of the channel.

In addition, the invention provides for the bulk photoproduction of H$_2$ using the transformed host cells of the invention.

Identification of the Residues that Form the H$_2$-Channel of a [Fe]-Hydrogenase The iron-hydrogenase family of enzymes is a group of enzymes expressed in algae for metabolism of hydrogen. Iron-hydrogenase family members have been shown to have three distinct motifs that contain highly conserved residues, including a series of identifiable cysteine residues. Vignais et al., (2001) FEMS Micro. Rev. 25:455-501. In particular, motif 1 has the amino acid sequence PMFTSCCPxW, motif 2 has an amino acid sequence MPCxxKxxExxR and motif 3 has an amino acid sequence of FxExMACxGxCV. These three motifs have been identified in all iron-hydrogenase family members to date. The cysteine residues have been shown to either ligate the catalytic [4Fe-4S] center, or bridge the [4Fe-4S] to the [2Fe-2S] center, and there presence within the primary structure of the enzyme is highly conserved. One of the most studied iron-hydrogenase enzymes is CpI, having its primary, secondary and tertiary structures determined. Peters et al., (1998) Science 282:1853-1858. In preferred embodiments, CpI or other like known iron-hydrogenase enzymes, can be used in the design and engineering of oxygen-resistant hydrogenases (see below and FIG. 1A for potential iron-hydrogenase enzymes).

To identify the H$_2$-channel within a target hydrogenase, i.e., a polypeptide containing motifs 1-3 above, the primary sequence of the target hydrogenase must be compared to the primary sequence of a known hydrogenase. Once the two sequences have been aligned a level of identity is determined (see FIG. 1A and 2). Stothard P., (2000) BioTechniques 28(6) 1102 (hereby incorporated by reference in its entirety). For purposes of the present invention an overall identity of approximately 40%-45% or better should be found for the target hydrogenase. Further, an analysis of the target polypeptide's primary sequence is performed to predict the sequences that share homology with the H$_2$-chanel forming regions of other known iron-hydrogenases (similar patterns of residues that have been shown previously to form hydrophobic cavities). Montet et al., (1997) Nat. Struc. Biol; 4:523-526. It should be noted that because the H$_2$-channel is a conserved domain within all hydrogenases, other non-iron hydrogenase sequences can be used to identify the target hydrogenase H$_2$-channel. There should be at least 40%-45% identity between the known and unknown sequence between the H$_2$-channel sequences of the know and unknown hydrogenases. Once the region within the target polypeptide for the H$_2$-channel has been located, the channel is modeled into a three-dimensional structure showing the orientation of residues in relation to the channel and active site. Guex et al., (1997) Electrophoresis 18:27142723. (see below) In some embodiments, the analysis is extended to identify the residues corresponding to the active site within the target hydrogenase. Note that the active site of the target or unknown hydrogenase should share at least 90% homology for motifs 1-3, and in preferred embodiments shown complete identity with motifs 1-3 (see above). The combination of primary and tertiary structures of the target hydrogenase are compared to evaluate the identification of candidate regions for the final verification of the hydrogen-channel.

Methods for Designing and Engineering Oxygen-resistant Iron-Hydrogenases

As noted above, the present invention provides a model for generating a theoretical structure of a target H$_2$-channel within a target hydrogenase enzyme. In one embodiment, the theoretical structure is generated by homology modeling (see above) to the solved structure of other known [Fe]-hydrogenases, for example CpI. (see FIG. 1A). In some embodiments, the homology modeling is limited to the known hydrogenase active site and H$_2$-channel, and in other embodiments the homology modeling can be limited to the known hydrogenase H2-channel sub-domains. A percent homology of the known hydrogenase (both identity and similarity) can be used to determined residue identity and similarity for the entire enzyme, the active site, the H2-channel and the H$_2$-channel sub-domains (see overhead arrows in FIG. 2 and see discussion in previous section above). As such, the present invention provides a known hydrogenase based homology model that gives a reliable approximation of the target hydrogenase structure and H$_2$-channel environment. In a preferred embodiment, the known hydrogenase is CpI and the target hydrogenase is HydAl. Homology modeling can be performed using Swiss-model software as described in Guex et al. Electrophoresis 18:2714-2723. Note, however, that other like programs can be used in this aspect, as is known in the art, e.g., Modeller program designed by Marti-Renom et al., (2000) Ann. Rev. Biophy, Biomol. Struct. 29:291-325; EsyPred3D designed by Lambert C. et al., (2002) Bioinformatics 18(9):1250-1256.

Typically, the homology modeling identifies the residues that project into the H$_2$-channel interior of the target hydrogenase. The channel environment is often composed of smaller hydrophobic residues, e.g., glycine, alanine, valine, but can contain phenylalanine and other like residues. For example, the H$_2$-channel of HydA1 contains mostly small hydrophobic residues with the exception of the larger phenylalanines at positions 252 and 355 (see FIG. 2, black dotted residues). A secondary structure is determined from the active site to the enzyme surface using the modeled structure above, and distances between side chain atoms of identified residues opposed to each other are determined. Guex et al., Supra An approximate average diameter of the channel over the distance from the catalytic site (Fe2-atom to the H-cluster [2Fe-2S]-center) to the protein surface is determined (see FIG. 3, 1-4) (typically by using the distances between the side chain atoms of opposed residues within the channel). It silico mutagenesis is performed on the identified hydrogenase H$_2$-channel structure to identify possible residues that can be modified to reduce the H$_2$-channel diameter. Mutagenesis criteria preferably involve conservative mutation of specific residues, selection of the lowest energy rotomer and energy minimization of the resulting structure using GROMOS. van Gunsteren, W. F. et al., (1996) Biomolecular Simulation, The GROMOS96 Manual and User Guide. Vdf Hochschulverlag ETHZ. Once an energy minimized structure is obtained, the dimensions of the target in silico mutagenized hydrogenase channel is determined. In preferred embodiments, one or more locations along the $H_2$-channel is designed via conservative mutation to be smaller in diameter than a corresponding non-mutated $H_2$-channel, typically this reduction is to a channel size of between approximately 5.0 and 2.4 Å in diameter, and preferably between 3.5 and 2.5 Å, a diameter that either limits or eliminates the ability of oxygen to diffuse through the modified $H_2$-channel. Note that the $H_2$-channel is in constant flux, as such diameter measurements are averages and not meant to be held to a static standard. Note that in embodiments of the present invention, more than one residue can be in silico mutated to design an optimum oxygen-resistant hydrogenase.

In an alternative embodiment, design of oxygen-resistant hydrogenase enzymes is provided by determining what substitutions/modifications of residues within the identified $H_2$-channel of a target [Fe]-hydrogenase can be performed to reduce the volume of the $H_2$-channel. Volume considerations include a reduction in the flow of gasses, i.e., $O_2$, through the channel in accordance with Stokes Einstein Equation and Fick's law.

Designed oxygen-resistant hydrogenases, having a reduced diameter $H_2$-channel, are genetically engineered and transformed into target host cells, for example, into *C. reinhardtii*, and tested for hydrogenase activity in the presence of $O_2$ via a modified Clark electrode or other known assay(s). In preferred embodiments, the oxygen-resistant hydrogenase is generated via site-directed mutagenesis. For example, to generate HydA1 mutants, the HydA1 gene of pA1 ExBle can be mutagenized in vitro using the Quick Change XL Site-Directed Mutagenesis Kit (Stratagene). Host cells that have incorporated the designed enzymes having reduced oxygen sensitivity) can be used to photoproduce $H_2$ in an oxygen containing environment. Note that these host cells can also be treated with mRNA interference to repress the expression of native hydrogenases, while continuing to allow expression of the inventive engineered hydrogenase(s).

Steered Molecular Dynamics (SMD)

In one embodiment, the in silico designed oxygen-resistant hydrogenase enzymes can be further analyzed for changed or reduced oxygen diffusion within their $H_2$-channel by applying SMD via the NAMD program. Kale L. et al., (1999) Computational Physics 151:283; Isralewitz B., (2001) Curr. Opin. Struc. Biol. 11:224. SMD analysis, therefore, provides confirmation and additional baseline data as to the efficiency of the channel modifications and their effects on $O_2$ diffusion within the proposed oxygen-resistant hydrogenase.

Oxygen-Resistant Hydrogenase Polypeptides

Oxygen-resistant hydrogenase enzymes of the invention include all proteins that can be constructed from the in silico mutagenesis methods discussed above. For example, any polypeptide having a predicted reduction in hydrogen-channel diameter or volume, as determined by the methods of the invention, is envisioned to be within the scope of the present invention.

In addition, oxygen-resistant hydrogenase enzymes of the invention include isolated polypeptides having an amino acid sequence as shown in FIG. 2 (Cr HydA1), and having one or more substitutions at residues V240, A78, A244, A248, G86, and L93 (note that substitution by tryptophan and other like amino acids is envisioned, including synthetic or derivatized amino acids) (also included are substitutions shown in Tables 1 and 2). The invention includes variants and derivatives of these oxygen-resistant [Fe]-hydrogenase enzymes, including fragments, having substantial identity to these amino acid sequences, and that retain both hydrogenase activity and enhanced tolerance to oxygen (see Example 3 for assays to determine hydrogenase activity in the presence of oxygen). In a preferred embodiment, the oxygen-resistant hydrogenase enzyme is HydA1V240W. Derivatives of the oxygen-resistant hydrogenases include, for example, oxygen-resistant HydA1 enzymes modified by covalent or aggregative conjugation with other chemical moieties, such as lipids, acetyl groups, glycosyl groups, and the like.

Oxygen-resistant hydrogenase enzymes of the present invention can be fused to heterologous polypeptides to facilitate purification. Many available heterologous peptides allow selective binding of the fusion protein to a binding partner, for example, 6-His, thioredoxin, hemaglutinin, GST, and the like.

Polypeptide fragments of the modified oxygen-resistant hydrogenase $H_2$-channel polypeptide (that include the relevant residue modification) can be used to generate specific anti-oxygen-resistant hydrogenase antibodies (monoclonal or polyclonal). Generated antibodies can be used to selectively identify expression of oxygen-resistant hydrogenases or in other known molecular and/or biochemical techniques, for example, in immunoprecipitation or Western blotting.

Variant oxygen-resistant hydrogenase enzymes include fusion proteins formed of a oxygen-resistant hydrogenase and a heterologous polypeptide. Preferred heterologous polypeptides include those that facilitate purification, stability or secretion.

Oxygen-Resistant Hydrogenase Polynucleotides, Vectors and Host Cells

The invention also provides polynucleotide molecules encoding the oxygen-resistant polypeptides of the invention. The polynucleotide molecules of the invention can be cDNA, chemically synthesized DNA, DNA amplified by PCR, RNA or combinations thereof.

The present invention also provides vectors containing the polynucleotide molecules of the invention, as well as host cells transformed with such vectors. Any of the polynucleotide molecules of the invention may be contained in a vector, which generally includes a selectable marker, and an origin of replication, for propogation in a host. The vectors also include suitable transcriptional or translational regulatory sequences, such as those derived from algae operably linked to the oxygen-resistant hydrogenase polynucleotide molecule. Examples of such regulatory sequences include transcriptional promoters, operators, enhances, and mRNA binding sites. Nucleotide sequences are operably linked when the regulatory sequence functionally relates to the DNA encoding the target protein. Thus, a promoter nucleotide sequence is operably linked to a oxygen-resistant hydrogenase DNA sequence if the promoter nucleotide sequence directs the transcription of the oxygen-resistant hydrogenase sequence.

Figure 8:
FIG. 8 shows a plasmid map for the plasmid pLam91-1.
Figure 9:
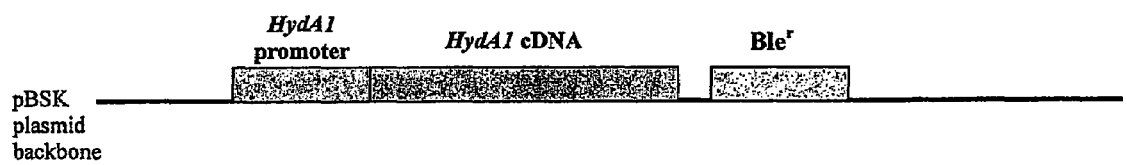
FIG. 9 shows a plasmid map for the plasmid pA1ExBle.

Selection of suitable vectors for the cloning of oxygen-resistant hydrogenase polynucleotides of the invention will depend on the host cell in which the vector will be transformed/expressed. For example, the plasmid pLam91-1 (see FIG. 8) was used to create a 980 bp HydA1 PstI promoter fragment cloned into a unique PstI site of pLam91-1, creating the HydA1 promoter-HydA1 cDNA fusion construct, pA1Ax. The Ble$^r$ cassette of pSP108 confers Bleomycin resistance in transformed *C. reinhardtii*, and was inserted into the TfiI site of pA1Ax, creating pA1AxBle (see FIG. 9). This was particularly useful in the construction of expression oxygen-resistant [Fe]-hydrogenase vectors for use in green algae.

Suitable host cells for expression of target polypeptides of the invention include green algae, for example *C. reinhardtii* cells and cyanobacteria, both of which utilize water in growth, which is also a substrate for the hydrogenase enzymes. Typically, green algae cells are transformed by a glass bead method as is known in the art. Cells exhibiting the target selectable marker, for example resistance to bleomycin, are picked and patched onto fresh TAP+Ble plates and re-patched an additional 2-3 times to ensure the isolation of stable integrates.

$H_2$ Production

Green algal cultures that express oxygen-resistant hydrogenase of the invention may be used to photoproduce $H_2$ in the presence of oxygen. In one embodiment of the invention, the transformed cells are grown in a photobioreactor photoautotrophically, photoheterotrophically in TAP, or other like growth media to a concentration of 5-50 μg/ml chlorophyll, and $H_2$ harvested. Note that in some embodiments, the cells are grown under selective pressure that ensures that the cells maintain the oxygen-resistant hydrogenase, for example in bleomycin, where the construct used to transform the host cell confers the selective pressure.

In another embodiment, the oxygen-resistant hydrogenase of the invention may be transformed into target algae, under the control of the endogenous HydA1 promoter, for nighttime enzyme generation and daytime $H_2$-production. See Boichenko et al., (2003) Photoconversion of Solar Energy, Molecular to Global Photosynthesis: In Press.

It is envisioned that the proceeding discussion on the design, engineering, and construction of oxygen-resistant hydrogenases, as well as the subsequent tansformation of host cells with the designed hydrogenases, can be expanded to any iron hydrogenase known or identified in the future having the characteristics for iron hydrogenase enzymes discussed herein.

Having generally described the invention, the same will be more readily understood by reference to the following examples, which are provided by way of illustration and are not intended as limiting.

EXAMPLES

Example 1

Computer Modeling of Hydrogenase $H_2$-Channel for Design of Oxygen-Resistant Hydrogenase Enzymes To facilitate the design and engineering of mutant oxygen-resistant HydA1 enzymes, a theoretical structure of HydA1 was generated by homology modeling to the solved X-ray structure of *Clostridium pasteuraianuin* [Fe]-hydrogenase, CpI (FIG. 1B). The theoretical model was generated by homology modeling using Swiss-model software as described by Guex et al., (1997) Electrophoresis 18:2714-2723. The resulting HydA1 model was subjected to several rounds of energy minimization using GROMOS. An alignment of the HydA1 and CpI amino acid sequences show they share a high degree of homology (45% identity, 58% similarity) within the essential domains, i.e., active site and $H_2$-channel, that comprise the core region of [Fe]-hydrogenases (see FIG. 2). Stothard P., (2000) BioTechniques 28(6) 1102. Note that the degree of conservation increases for $H_2$-channel subdomains, where the two proteins share 62% identity and 92% similarity (FIG. 2, overhead arrows). This high level of sequence identity/similary shows that the CPI-based HydA1 homology model provides a resonable approximation of the HydA1 structure and the $H_2$-channel environment. HydA1 homology model provides a reasonable approximation of the HydA1 structure and the $H_2$-channel environment.

The detailed study of the HydA1 $H_2$-channel structure was performed, at least partly, to identify residues that project into the $H_2$-channel interior. In general, the channel environment was primarily composed of smaller hydrophobic residues, e.g., glycine, alanine, valine, with the exception of the larger phenylalanines at positions 252 and 355 (FIG. 2, black dotted residues). The secondary structure of the $H_2$-channel was organized into two α-helices and two β-sheets, which extend from the active site to the enzyme surface. The distance between side chain atoms of residues that oppose each other were measured to approximate the average channel diameter over the distance from the catalytic site (Fe2-atom of the H-cluster [2Fe-2S]-center) to the protein surface (1 to 4, FIG. 3). The channel measured 3.85 to 7.44 Å in diameter over a distance of 24 to 27 Å, making the channel diameter greater than the effective diameters of both $H_2$ (2.8 Å) and $O_2$ (3.5 Å). As a result, the predicted size of the HydA1 $H_2$-channel is sufficient to function in H2 diffusion from the active site to the surface, but it is also large enough to allow for the inward diffusion of the inhibitor $O_2$.

These results suggest that engineering $O_2$ tolerance into HydA1 might be accomplished by altering the residues that line the interior of the channel so as to reduce the diameter of the channel and thereby limit $O_2$ diffusion to the active site. The potential to reduce the diameter of the channel via residue substitution was initially tested in silico by mutating the $H_2$-channel of the HydA1 model. The mutagenesis criteria involved conservative mutation, i.e., hydrophobic→hydrophobic, of specific residues, selection of the lowest energy rotomer, and energy minimization of the resulting structure using GROMOS. Once an energy-minimized structure was obtained, the dimensions of its channel was determined. Several of the channel residues proved to be unameanable to mutation and were left unchanged, i.e., 182, L89, F252 and F355, i.e., the Guex program determined that changes at these locations would provide only minimal (non-significant) change to the $H_2$-channel diameter/volume. However, promising mutants were generated from alteration of several residues that were spaced over the entire length of the channel (see FIG. 2 and Table 1). Substantial reductions of channel diameter were obtained by mutating residues A78 and V240 (proximal to active site); A244, A248 and G86 (mid-channel);

and L93 (protein-solvent boundary, distal to active site) to bulkier amino acids (Table 1 and FIG. 3). The individual mutations listed in Table 1 caused reductions in diameter that ranged from 0.5 to 1.90 Å (Table 2). The HydA1 mutant that combined the A248I and L93F mutations located at the channel-solvent boundary (FIG. 3, zone 4) showed an average decrease in size from 5.21 to 3.34 ÅA, less than the effective diameter of $O_2$ (3.5 Å). When the mutations listed in Table 2 were combined into a single HydA1 mutant, the average overall channel diameter was reduced from an average 5.71 to an average of 4.31 Å (Table 2), noting however that there are several locations along the $H_2$-channel with reductions in the diameter at or near the average diameter of $O_2$.

TABLE 1

Predicted Effects of Selected HydA1 H2-Channel Mutations on Channel Environment

| Mutation | Location | Effects |
|---|---|---|
| A78I | Adjacent to $Fe_2$-atom, across from V240 | Bulkier isoleucine side chain projects closer to V240, and the [2Fe—2S]-center $Fe_2$ atom. |
| V240W | Adjacent to A78, above $Fe_2$-atom. | Bulkier tryptophan side chain reduces distance to A78, and partially shields $Fe_2$-atom. |
| A244L | Mid-channel, opposes I82 | Bulkier leucine side chain projects further into channel. |
| G86I | Mid-channel, opposes A248 | Isoleucine side chain adds bulk, and projects into channel. |
| A248I | Mid-channel, near surface, opposes G86 and L89 | Isoleucine extends further into channel, adds more bulk to hydrophobic surface. |
| L93F | Channel-Surface boundary | Narrows the channel opening at protein surface-solvent boundary |

TABLE 2

Distances Between Channel Determinants In HydA1 and HydA1 Mutants Based on Modeling Studies

| Zone[a] | Determinant Pairs[b] | Distances (Å) | | Average Zone Size (Å) | |
|---|---|---|---|---|---|
| | | HydA1 wild type | HydA1 mutant[c] | HydA1 wild type | HydA1 mutant[c] |
| 1 | A(I)78::$Fe_2$ | 6.25 | 4.66 | 6.90 | 5.04 |
| | V(W)240::$Fe_2$ | 6.14 | 5.02 | | |
| | V(W)240::A(I)78 | 7.43 | 5.43 | | |
| 2 | A(L)244::I82 | 4.50 | 3.90 | 5.30 | 4.87 |
| | F355::G(I)86 | 6.86 | 5.80 | | |
| 3 | G(I)86::A(I)248 | 4.38 | 3.54 | 5.42 | 3.92 |
| | G(I)86::T247 | 6.01 | 4.39 | | |
| | A(I)248::L89 | 3.85 | 3.26 | | |
| | A(I)248::F355 | 7.44 | 4.54 | | |
| 4 | L90::A(I)248 | 6.11 | 3.67 | 5.21 | 3.34 |
| | L(F)93::F252 | 4.31 | 3.01 | | |

[a]The locations of H2-channel zones are identified in FIG. 3.
[b]Determinants are identified as wild-type, with corresponding mutations in parentheses.
[c]Measurements are averages of a HydA1 mutant possessing all the identified mutations within the designated zone.

The above results indicate that modeling of the HydA1 structure has revealed a hydrophobic channel extending from the active site to the enzyme surface. This channel would appear to be conserved in other [Fe]-hydrogenases. The channel's secondary structure is mainly a-helical, which suggests that the channel domain is fairly rigid. Perhaps the rigidity of the channel structure helps to prevent its collapse during folding. Volbeda et al., (2002) Int. J. Hyd. Energy 27:1449-1461. Rigidity would also be expected to contribute to conformational stability of the channel in the folded protein, and a static model should give reasonable approximations of shape and size. Our measurements of the HydA1 channel demonstrate that it is sufficient in diameter not only to allow for diffusion of the product $H_2$ but also the larger-sized inhibitors $O_2$ and CO. Since enzyme inhibition occurs quickly (minutes), following exposure of $O_2$ (Happe et al., (1994) Eur. J. Biochem. 222:769-774), the channel would not appear to be highly restrictive to inhibitor diffusion, which is in agreement with our analysis. This data illustrates the utility of the present invention for engineering $O_2$-resistant, [Fe]-hydrogenase by manipulation of residues within the conserved $H_2$ channel. This modeling approach can be used in enzymes that have one channel or multiple channels to reduce inhibitor access to an enzyme active site.

Example 2

*C. reinhardtii* can be Transformed with HydA1 $H_2$-Channel Mutants

To test the ability of the predicted HydA1 $H_2$-channel mutants for limiting $O_2$ inhibition, an algal HydA1 expression system was created using the HydA1 endogenous promoter. From the modeling discussed in Example 1, the V240W mutation was selected for further examination. In vivo expression of the V240W mutant was performed and further testing of the mutant for $O_2$ resistance hydrogenase activity performed. Note that the V240W mutation is predicted to cause a constriction of the channel near the active site (see FIG. 4). In addition, the tryptophan projects over the $Fe_2$-atom, partially shielding it from the channel domain.

The *Chlamydomonas reinhardtii* strain cc849 (cw10, mt-) was used as the wild type parent strain throughout the remainder of this Example. Growth of liquid cultures were performed photoheterotrophically in TAP medium (Harris E, (1989) The Chlamydomonas Source Book, Academic Press, New York) with a continuous stream of 5% $CO_2$ under cool-white fluorescent light (150 $\mu E/m^{-2}/s^{-1}$ PAR). Growth on solid medium was performed on TAP agar plates (TAP medium with 1.4% w/v agar). Note that when selection of Bleomycin resistance was performed, solid TAP medium was supplemented with 10 µg/ml Zeocin (Invitrogen).

A plasmid construct pLam91-1, containing the HydA1 cDNA and 3'-terminator regions cloned into the EcoRI-XhoI sites of pBluescript SK, was used to generate an algal HydA1 expression construct. A 980 bp HydA1 PstI promoter fragment was cloned into the unique PstI site of Lam91-1, creating the HydA1 promoter-HydA1 cDNA fusion construct, pA1Ex. The Ble[r] cassette of pSP108 that confers Bleomycin resistance in transformed *C. reinhardtii* (Stevens et al., (1996) Mol Gen Genet 251:23-30) was inserted into the TfiI site of pA1Ex, creating pA1ExBle.

Site-directed mutagenesis was performed on HydA1 to generate HydA1 mutants for expression in *C. reinhardtii*. The HydA1 gene pA1ExBle was mutagenized in vitro using the Quick Change XL Site-Directed Mutagenesis Kit of Stratagene. Oligonucleotides (Integrated DNA Technologies) used for mutagenesis were designed based on the kit requirements. Mutant pA1ExBle constructs were sequenced to confirm the presence of individual mutations. The HydA1 mutant, V240W, contains a valine to tryptophan substitution at amino acid position 240 of the mature protein.

*C. reinhardtii* cells were next transformed by the glass bead method as is known in the art (see also Harris E) using 10 µg of linearized pA1ExBleV240W DNA. Following transformation, cells were cultured overnight in 2 ml of TAP medium to allow for cell recovery and phenotypic expression of Ble[r]. Transformed cells were harvested by centrifugation (2000×g, 5 minutes), resuspended in 1.5 ml TAP soft agar (TAP with 0.8% w/v agar) and spread onto TAP+Ble agar plates. Plates were incubated in the light for a period of 1-2 weeks and Ble[r] colonies picked. Resistant colonies were patched onto fresh TAP+Ble plates, and re-patched an additional 2-3 times to ensure the isolation of stable integrates.

Figure 5:
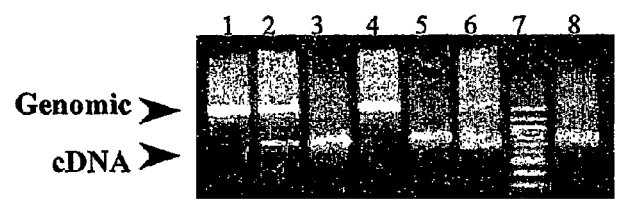
FIG. 5 illustrates PCR products from *C. reinhardtii* HydA1V240W transformants mt18 and mt28. Genomic DNA isolated from cc849 (wild type), mt18, and mt28 were digested with either SacI (lanes 1-3) or EcoRI (lanes 4-6) and used as template in a PCR reaction with HydA1 specific primers. Lanes 1 and 4 are wild type, lanes 2 and 5 are mt18 and lanes 3 and 6 are mt28. Note that lane 7 is a DNA size marker and lane 8 is a pAExBle control. The upper band in the stained agarose gel corresponds to the HydA1 genomic copy, and the lower band corresponds to the HydA1 cDNA insert.

To ensure that the HydA1 cDNA genomic insert having the V240W mutation was present in the transformed *C. reinhardtii*, PCR and sequencing was performed on Ble$^r$ transformants. Total genomic DNA was isolated from individual Ble$^r$ transformants using the Plant Genomic Kit (Qiagen). A total of 0.5 to 1.0 μg of purified genomic DNA was digested with either SacI or EcoRI and used as template in a PCR reaction consisting of the HydA1 internal primers (5'- CACGCT-GTTTGGCAT CGACCTGACCATCATG-3'JSEQ ID NO: 8) and 5'- GCCACGGCCACGCGGAATGTGATG CCGC-CCC-3'JSEQ ID NO: 9)), 1 unit KOD HotStart polymerase (Novagen), 10 mM $MgSO_4$, 25 mM of each dNTP, 2% DMSO (v/v), and water to a total volume of 50 μl. The presence of a HydA1 cDNA genomic insert results in an additional 780 bp HydA1 cDNA product together with the 1120 bp HydA1 genomic product. PCR reactions were run on 1×TAE agarose gels (1.25% agarose w/v), stained with ethidium bromide, and photographed (not shown). The 780 bp band, corresponding to the HydA1 cDNA insert, was purified and sequenced to confirm the presence of V240W mutation. Two Ble$^r$*C. reinhardtii* clones, mt18 and mt28, were shown to possess the HydA1V240W construct (see FIG. 5).

Example 3

Green Alga, *C. reinhardtii*, Transformed with Oxygen-Resistant Hydrogenases are Effective In The Bulk Production of $H_2$ The $O_2$-sensitivity of [Fe]-hydrogenase activity in strains mt18 and mt28 carrying the HydA1V240W mutation was tested in either whole cells or whole cell extracts of anaerobically induced cultures. Hydrogenase activities were measured as $H_2$ gas photoproduction by whole cells as previously described. Ghirardi et al., (1997) App. Biochem. Biotech. 63-65:141-151; Flynn et al., (2002) Int. J. Hyd Energy 27:1421-1430. Briefly, cells were grown photoheterotrophically in TAP to a concentration of 15-20 μg/ml chlorophyll, harvested and resuspended at 200 μg/ml chlorophyll in phosphate induction buffer. Ghirardi et al. Clark electrode measurement of $O_2$-resistant hydrogenase activity was performed by adjusting the $O_2$ concentration in the electrode chamber to a set level between 0% and 4%. Once the $O_2$ level had stabilized, a stream of Ar gas was passed over the chamber to maintain a constant $O_2$ concentration. A 0.2 ml sample of induced cell suspension was injected into the chamber, and the cells kept in the dark for a two minute period. Light dependent $H_2$-photoproduction activity was then induced by illumination.

In addition, to measure hydrogenase activity directly, reduced methyl viologen (MV) was used as an artificial electron donor for $H_2$ production by solubilizing whole cells as previously described. Flynn et al. Tolerance to $O_2$ was measured by incubating 1 ml of induced cells in a dark, sealed glass bottle and injecting $O_2$ to achieve a final atmosphere of 1 to 4% (v/v). Samples were incubated for two minutes then purged with Ar gas for five minutes. A 1 ml mixture of reduced MV and Triton X-100 in a phosphate buffer was added, samples were mixed for three to five minutes, and 0.1 ml of 100 mM reduced Na-dithionite injected to start the reaction. The reaction mixtures were incubated for 30 minutes at room temperature with stirring, and reactions were stopped by the addition of 0.1 ml 20% trichloroacetic acid (TCA). The hydrogen content of a 0.2 ml headspace sample was measured by gas chromatograph. Three separate headspace samples were assayed, and the values were averaged to attain final hydrogen-production rates.

As shown in Table 3. all three strains, cc849, mt18, and mt28, exhibited similar levels of hydrogenase activity (rate of $H_2$ photoproduction) under completely anaerobic conditions. Note that as has been shown in previous studies (Ghirardi et al, supra; Flynn et al, supra), pretreatment of induced wild type cells with $O_2$ is sufficient to cause a significant decline in H2 production rate (FIG. 6, white bars). When induced wild-type cells were pre-treated with $O_2$ at a concentration of 1.7 to 3.5%, the H2 photoproduction rate declined by 90 to 100% respectively. However, the exposure of mt18 or mt28 induced cells to similar $O_2$ treatments showed H2 photoproduction activity had significant resistance to inactivation. After exposure to 1.7 to 2.2% $O_2$ concentrations, the $H_2$ photoproduction rates remained 3.8 to 7 fold higher in mt18, and 3.2 to 13 fold higher in mt28 compared to activities in wild-type cells under identical conditions (see FIG. 6). At 3.5% $O_2$ treatment, the H2 photoproduction rates in both mt18 and mt 28 were low, but detectable, whereas residual activity in wild-type cells was undetectable (FIG. 6).

TABLE 3

Hydrogenase Activity By the Clark Electrode Assay

| Strain | H$_2$ Photoproduction Rate (μmol H2/mg chl$^{-1}$/h$^{-1}$) |
|---|---|
| cc849 | 10.4 |
| mt18 | 14.1 |
| mt28 | 10.7 |

The light-induced production of hydrogen by whole cells is a metabolic process and depends on many electron transfer steps. Zhang et al., (2000) Trends Biotech. 18(12):506-511; Melis et al., (2001) Plant Physiol. 127:740-748; Melis et al., (2000) Plant Physiol. 122:127-135. A more direct measurement of hydrogenase activity can be accomplished in solubilized whole cells using reduced MV ($Mv_{red}$) as electron donor for H2 gas production by hydrogenase in the dark. Under completely anaerobic conditions, the $Mv_{red} \rightarrow H_2$ reaction rates were similar in value for either induced wild-type or mutant cells (see Table 4). As shown in FIG. 7, a two-minute exposure of induced wild-type to various $O_2$ concentrations caused hydrogenase activity to decline. After exposure of $O_2$ concentrations of 1% to 4% hydrogenase activities in wild-type cells decreased to between 10 and 1.5% respectively (FIG. 7), similar to the results shown in FIG. 6. In comparison, both mtl6 and mt28 containing the HydA1V240W construct exhibited significant levels of $O_2$ resistant hydrogenase activity (see FIG. 7). Exposure of mt18 to $O_2$ at 1% to 4% concentration caused hydrogenase activities to decline by 76% to 96%, whereas mt28 activities declined only 12% to 76% (FIG. 7). As a result, mt18 hydrogenase activities were 2- to 3-fold higher, and mt28 activities 8- to 15-fold higher than activities in wild-type cells after exposure to similar $O_2$ treatments.

TABLE 4

Hydrogenase Activity By the Methyl Viologen Assay

| Strain | H2 Photoproduction Rate (μmol H2/mg chl$^{-1}$/h$^{-1}$) |
|---|---|
| cc849 | 31.3 |
| mt18 | 32.9 |
| mt28 | 35.5 |

This Example illustrated the utility of modeling residue substitutions within the $H_2$-channel to constrict the channel from $O_2$ passage to the [2Fe-2S]-center. In particular, the Example illustrated that substitution of tryptophan for valine at position 240 of HydA1 caused an increase tolerance to $O_2$ in the mutant hydrogenase. The difference in the structure change made to HydA1V240W and the effects of that change are similar to the observed differences in structure and $O_2$-resistance of $H_2$-sensing [NiFe]-hydrogenases compared to catalytic [NiFe]-hydrogenases. Volbeda et al., (2002) Int. J. Hyd. Energy 27:1449-1461; Bernhard et al., (2001) 276: 15592-15597. Active-site proximal channel residues of $O_2$-resistant, $H_2$-sensing [NiFe]-hydrogenases contain the bulky, hydrophobic amino acids isoleucine and phenylalanine. Identical positions in the $O_2$-sensitive, catalytic [NiFe]-hydrogenases encode the smaller-sized residues valine and leucine respectively. The difference in amino acid composition is suggested to result in the shielding of the [NiFe]-cluster and constriction of the channel. Volbeda supra and Bernhard supra.

The invention has been described with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to patents and publications. Each is hereby incorporated by reference in their entirety for all purposes.

The invention claimed is:

1. A *Chlamydomonas reinhardtii* oxygen-sensitive iron hydrogenase variant which is mutated by substitution of one or more identified amino acid residues within a hydrogen channel of the oxygen-sensitive iron hydrogenase, wherein the one or more identified amino acid residues are independently substituted with an amino acid selected from the group consisting of tryptophan, isoleucine, leucine and phenylalanine, having properties that limit $O_2$ diffusion through the channel while allowing $H_2$ diffusion out of the channel, and wherein the substituted amino acid reduces the diameter of the channel, wherein the variant hydrogenase is an oxygen-resistant iron hydrogenase.

2. The oxygen-resistant iron hydrogenase of claim 1, wherein the one or more residues within the hydrogen channel of the oxygen-sensitive iron hydrogenase are independently substituted with at least one bulky residue that projects close to a catalytic site having a bimetallic center containing two iron atoms.

3. The oxygen-resistant iron hydrogenase of claim 1, wherein the one or more residues within the hydrogen channel of the oxygen-sensitive iron hydrogenase are independently substituted with at least one bulky residue that partially shields an $Fe_2$-atom.

4. The oxygen-resistant iron hydrogenase of claim 1, wherein the one or more residues within the hydrogen channel of the oxygen-sensitive iron hydrogenase are independently substituted with leucine and/or isoleucine that projects into the hydrogen channel.

5. The oxygen-resistant iron hydrogenase of claim 1, wherein the one or more residues within the hydrogen channel of the oxygen-sensitive iron hydrogenase are independently substituted with at least one bulky residue that narrows the channel opening at a protein surface-solvent boundary.

6. The oxygen-resistant iron hydrogenase of claim 1, wherein the average channel size is between about 5.0 and about 2.4 Å in diameter.

7. The oxygen-resistant iron hydrogenase of claim 1, wherein the average channel size is between about 3.5 and about 2.4 Å in diameter.

* * * * *

SEQUENCE LISTING

<160> NUMBER OF SEQ ID NOS: 9

<210> SEQ ID NO 1
<211> LENGTH: 333
<212> TYPE: PRT
<213> ORGANISM: Chlamydomonas reinhardtii

<400> SEQUENCE: 1

```
Pro Val Ala Ala Leu Lys Glu Lys Ser His Ile Glu Lys Val Gln Glu
1               5                   10                  15

Ala Leu Asn Asp Pro Lys Lys His Val Ile Val Ala Met Ala Pro Ser
                20                  25                  30

Val Arg Thr Ala Met Gly Glu Leu Phe Lys Met Gly Tyr Gly Lys Asp
            35                  40                  45

Val Thr Gly Lys Leu Tyr Thr Ala Leu Arg Met Leu Gly Phe Asp Lys
        50                  55                  60

Val Phe Asp Ile Asn Phe Gly Ala Asp Met Thr Ile Met Glu Glu Ala
65                  70                  75                  80

Thr Glu Leu Leu Gly Arg Val Lys Asn Asn Gly Pro Phe Pro Met Phe
                85                  90                  95

Thr Ser Cys Cys Pro Ala Trp Val Arg Leu Ala Gln Asn Tyr His Pro
                100                 105                 110

Glu Leu Leu Asp Asn Leu Ser Ser Ala Lys Ser Pro Gln Gln Ile Phe
            115                 120                 125

Gly Thr Ala Ser Lys Thr Tyr Tyr Pro Ser Ile Ser Gly Ile Ala Pro
        130                 135                 140

Glu Asp Val Tyr Thr Val Thr Ile Met Pro Cys Asn Asp Lys Lys Tyr
145                 150                 155                 160

Glu Ala Asp Ile Pro Phe Met Glu Thr Asn Ser Leu Arg Asp Ile Asp
                165                 170                 175

Ala Ser Leu Thr Thr Arg Glu Leu Ala Lys Met Ile Lys Asp Ala Lys
            180                 185                 190

Ile Lys Phe Ala Asp Leu Glu Asp Gly Glu Val Asp Pro Ala Met Gly
        195                 200                 205

Thr Tyr Ser Gly Ala Gly Ala Ile Phe Gly Ala Thr Gly Gly Val Met
    210                 215                 220

Glu Ala Ala Ile Arg Ser Ala Lys Asp Phe Ala Glu Asn Lys Glu Leu
225                 230                 235                 240

Glu Asn Val Asp Tyr Thr Glu Val Arg Gly Phe Lys Gly Ile Lys Glu
```

```
                    245                 250                 255
Ala Glu Val Glu Ile Ala Gly Asn Lys Leu Asn Val Ala Val Ile Asn
                260                 265                 270
Gly Ala Ser Asn Phe Phe Glu Phe Met Lys Ser Gly Lys Met Asn Glu
            275                 280                 285
Lys Gln Tyr His Phe Ile Glu Val Met Ala Cys Pro Gly Gly Cys Ile
        290                 295                 300
Asn Gly Gly Gly Gln Pro His Val Asn Ala Leu Asp Arg Glu Asn Val
305                 310                 315                 320
Asp Tyr Arg Lys Leu Arg Ala Ser Val Leu Tyr Asn Gln
                325                 330

<210> SEQ ID NO 2
<211> LENGTH: 333
<212> TYPE: PRT
<213> ORGANISM: Chlamydomonas reinhardtii

<400> SEQUENCE: 2

Pro Val Ala Ala Leu Ser Glu Lys Ser His Met Asp Arg Val Lys Asn
1               5                   10                  15
Ala Leu Asn Ala Pro Glu Lys His Val Ile Val Ala Met Ala Pro Ser
                20                  25                  30
Val Arg Ala Ser Ile Gly Glu Leu Phe Asn Met Gly Phe Gly Val Asp
            35                  40                  45
Val Thr Gly Lys Ile Tyr Thr Ala Leu Arg Gln Leu Gly Phe Asp Lys
        50                  55                  60
Ile Phe Asp Ile Asn Phe Gly Ala Asp Met Thr Ile Met Glu Glu Ala
65                  70                  75                  80
Thr Glu Leu Val Gln Arg Ile Glu Asn Asn Gly Pro Phe Pro Met Phe
                85                  90                  95
Thr Ser Cys Cys Pro Gly Trp Val Arg Gln Ala Glu Asn Tyr Tyr Pro
            100                 105                 110
Glu Leu Leu Asn Asn Leu Ser Ser Ala Lys Ser Pro Gln Gln Ile Phe
        115                 120                 125
Gly Thr Ala Ser Lys Thr Tyr Tyr Pro Ser Ile Ser Gly Leu Asp Pro
    130                 135                 140
Lys Asn Val Phe Thr Val Thr Val Met Pro Cys Thr Ser Lys Lys Phe
145                 150                 155                 160
Glu Ala Asp Arg Pro Gln Met Glu Lys Asp Gly Leu Arg Asp Ile Asp
                165                 170                 175
Ala Val Ile Thr Thr Arg Glu Leu Ala Lys Met Ile Lys Asp Ala Lys
            180                 185                 190
Ile Pro Phe Ala Lys Leu Glu Asp Ser Glu Ala Asp Pro Ala Met Gly
        195                 200                 205
Glu Tyr Ser Gly Ala Gly Ala Ile Phe Gly Ala Thr Gly Gly Val Met
    210                 215                 220
Glu Ala Ala Leu Arg Ser Ala Lys Asp Phe Ala Glu Asn Ala Glu Leu
225                 230                 235                 240
Glu Asp Ile Glu Tyr Lys Gln Val Arg Gly Leu Asn Gly Ile Lys Glu
                245                 250                 255
Ala Glu Val Glu Ile Asn Asn Lys Tyr Asn Val Ala Val Ile Asn
                260                 265                 270
Gly Ala Ser Asn Leu Phe Lys Phe Met Lys Ser Gly Met Ile Asn Glu
            275                 280                 285
```

```
Lys Gln Tyr His Phe Ile Glu Val Met Ala Cys His Gly Gly Cys Val
        290                 295                 300

Asn Gly Gly Gly Gln Pro His Val Asn Pro Lys Asp Leu Glu Lys Val
305                 310                 315                 320

Asp Ile Lys Lys Val Arg Ala Ser Val Leu Tyr Asn Gln
                325                 330

<210> SEQ ID NO 3
<211> LENGTH: 321
<212> TYPE: PRT
<213> ORGANISM: Chlamydomonas reinhardtii

<400> SEQUENCE: 3

Pro Glu Asn Ala Ile Tyr Glu Ala Gln Ser Trp Val Pro Val Glu
1               5                   10                  15

Lys Lys Leu Lys Asp Gly Lys Val Lys Cys Ile Ala Met Pro Ala Pro
                20                  25                  30

Ala Val Arg Tyr Ala Leu Gly Asp Ala Phe Gly Met Pro Val Gly Ser
            35                  40                  45

Val Thr Thr Gly Lys Met Leu Ala Ala Leu Gln Lys Leu Gly Phe Ala
        50                  55                  60

His Cys Trp Asp Thr Glu Phe Thr Ala Asp Val Thr Ile Trp Glu Glu
65                  70                  75                  80

Gly Ser Glu Phe Val Glu Arg Leu Thr Lys Lys Ser Asp Met Pro Leu
                85                  90                  95

Pro Gln Phe Thr Ser Cys Cys Pro Gly Trp Gln Lys Tyr Ala Glu Thr
                100                 105                 110

Tyr Tyr Pro Glu Leu Leu Pro His Phe Ser Thr Cys Lys Ser Pro Ile
            115                 120                 125

Gly Met Asn Gly Ala Leu Ala Lys Thr Tyr Gly Ala Glu Arg Met Lys
130                 135                 140

Tyr Asp Pro Lys Gln Val Tyr Thr Val Ser Ile Met Pro Cys Ile Ala
145                 150                 155                 160

Lys Lys Tyr Glu Gly Leu Arg Pro Glu Leu Lys Ser Ser Gly Met Arg
                165                 170                 175

Asp Ile Asp Ala Thr Leu Thr Thr Arg Glu Leu Ala Tyr Met Ile Lys
            180                 185                 190

Lys Ala Gly Ile Asp Phe Ala Lys Leu Pro Asp Gly Lys Arg Asp Ser
        195                 200                 205

Leu Met Gly Glu Ser Thr Gly Gly Ala Thr Ile Phe Gly Val Thr Gly
        210                 215                 220

Gly Val Met Glu Ala Ala Leu Arg Phe Ala Tyr Glu Ala Val Thr Gly
225                 230                 235                 240

Lys Lys Pro Asp Ser Trp Asp Phe Lys Ala Val Arg Gly Leu Asp Gly
                245                 250                 255

Ile Lys Glu Ala Thr Val Asn Val Gly Gly Thr Asp Val Lys Val Ala
            260                 265                 270

Val Val His Gly Ala Lys Arg Phe Lys Gln Val Cys Asp Asp Val Lys
        275                 280                 285

Ala Gly Lys Ser Pro Tyr His Phe Ile Glu Tyr Met Ala Cys Pro Gly
        290                 295                 300

Gly Cys Val Cys Gly Gly Gly Gln Pro Val Met Pro Gly Val Leu Glu
305                 310                 315                 320

Ala
```

<210> SEQ ID NO 4
<211> LENGTH: 393
<212> TYPE: PRT
<213> ORGANISM: Chlamydomonas reinhardtii

<400> SEQUENCE: 4

```
Ala Thr Asp Ala Val Pro His Trp Lys Leu Ala Leu Glu Glu Leu Asp
1               5                   10                  15

Lys Pro Lys Asp Gly Gly Arg Lys Val Leu Ile Ala Gln Val Ala Pro
            20                  25                  30

Ala Val Arg Val Ala Ile Ala Glu Ser Phe Gly Leu Ala Pro Gly Ala
        35                  40                  45

Val Ser Pro Gly Lys Leu Ala Ala Gly Leu Arg Ala Leu Gly Phe Asp
    50                  55                  60

Gln Val Phe Asp Thr Leu Phe Ala Ala Asp Leu Thr Ile Met Glu Glu
65                  70                  75                  80

Gly Thr Glu Leu Leu His Arg Leu Lys Glu His Leu Glu Ala His Pro
                85                  90                  95

His Ser Asp Glu Pro Leu Pro Met Phe Thr Ser Cys Cys Pro Gly Trp
            100                 105                 110

Val Ala Met Met Glu Lys Ser Tyr Pro Glu Leu Ile Pro Phe Val Ser
        115                 120                 125

Ser Cys Lys Ser Pro Gln Met Met Gly Ala Met Val Lys Thr Tyr
    130                 135                 140

Leu Ser Glu Lys Gln Gly Ile Pro Ala Lys Asp Ile Val Met Val Ser
145                 150                 155                 160

Val Met Pro Cys Val Arg Lys Gln Gly Glu Ala Asp Arg Glu Trp Phe
                165                 170                 175

Cys Val Ser Glu Pro Gly Val Arg Asp Val Asp His Val Ile Thr Thr
            180                 185                 190

Ala Glu Leu Gly Asn Ile Phe Lys Glu Arg Gly Ile Ile Leu Pro Glu
        195                 200                 205

Leu Pro Asp Ser Asp Trp Asp Gln Pro Leu Gly Leu Gly Ser Gly Ala
    210                 215                 220

Gly Val Leu Phe Gly Thr Thr Gly Gly Val Met Glu Ala Ala Val Arg
225                 230                 235                 240

Thr Ala Tyr Glu Ile Val Thr Lys Glu Pro Leu Pro Arg Leu Asn Leu
                245                 250                 255

Ser Glu Val Arg Gly Leu Asp Gly Ile Lys Glu Ala Ser Val Thr Leu
            260                 265                 270

Val Pro Ala Pro Gly Ser Lys Phe Ala Glu Leu Val Ala Ala Arg Leu
        275                 280                 285

Ala His Lys Val Glu Glu Ala Ala Ala Glu Ala Ala Ala Val
    290                 295                 300

Glu Gly Ala Val Lys Pro Pro Ile Ala Tyr Asp Gly Gln Gly Phe
305                 310                 315                 320

Ser Thr Asp Asp Gly Lys Gly Gly Leu Lys Leu Arg Val Ala Val Ala
                325                 330                 335

Asn Gly Leu Gly Asn Ala Lys Lys Leu Ile Gly Lys Met Val Ser Gly
            340                 345                 350

Glu Ala Lys Tyr Asp Phe Val Glu Ile Met Ala Cys Pro Ala Gly Cys
        355                 360                 365

Val Gly Gly Gly Gly Gln Pro Arg Ser Thr Asp Lys Gln Ile Thr Gln
    370                 375                 380
```

Lys Arg Gln Ala Ala Leu Tyr Asp Leu
385                 390

<210> SEQ ID NO 5
<211> LENGTH: 386
<212> TYPE: PRT
<213> ORGANISM: Chlamydomonas reinhardtii

<400> SEQUENCE: 5

Ala Glu Ala Pro Leu Ser His Val Gln Gln Ala Leu Ala Glu Leu Ala
1               5                   10                  15

Lys Pro Lys Asp Asp Pro Thr Arg Lys His Val Cys Val Gln Val Ala
            20                  25                  30

Pro Ala Val Arg Val Ala Ile Ala Glu Thr Leu Gly Leu Ala Pro Gly
        35                  40                  45

Ala Thr Thr Pro Lys Gln Leu Ala Glu Gly Leu Arg Arg Leu Gly Phe
    50                  55                  60

Asp Glu Val Phe Asp Thr Leu Phe Gly Ala Asp Leu Thr Ile Met Glu
65                  70                  75                  80

Glu Gly Ser Glu Leu Leu His Arg Leu Thr Glu His Leu Glu Ala His
                85                  90                  95

Pro His Ser Asp Glu Pro Leu Pro Met Phe Thr Ser Cys Cys Pro Gly
            100                 105                 110

Trp Ile Ala Met Leu Glu Lys Ser Tyr Pro Asp Leu Ile Pro Tyr Val
        115                 120                 125

Ser Ser Cys Lys Ser Pro Gln Met Met Leu Ala Ala Met Val Lys Ser
    130                 135                 140

Tyr Leu Ala Glu Lys Lys Gly Ile Ala Pro Lys Asp Met Val Met Val
145                 150                 155                 160

Ser Ile Met Pro Cys Thr Arg Lys Gln Ser Glu Ala Asp Arg Asp Trp
                165                 170                 175

Phe Cys Val Asp Ala Asp Pro Thr Leu Arg Gln Leu Asp His Val Ile
            180                 185                 190

Thr Thr Val Glu Leu Gly Asn Ile Phe Lys Glu Arg Gly Ile Asn Leu
        195                 200                 205

Ala Glu Leu Pro Glu Gly Glu Trp Asp Asn Pro Met Gly Val Gly Ser
    210                 215                 220

Gly Ala Gly Val Leu Phe Gly Thr Thr Gly Gly Val Met Glu Ala Ala
225                 230                 235                 240

Leu Arg Thr Ala Tyr Glu Leu Phe Thr Gly Thr Pro Leu Pro Arg Leu
                245                 250                 255

Ser Leu Ser Glu Val Arg Gly Met Asp Gly Ile Lys Glu Thr Asn Ile
            260                 265                 270

Thr Met Val Pro Ala Pro Gly Ser Lys Phe Glu Glu Leu Leu Lys His
        275                 280                 285

Arg Ala Ala Arg Ala Glu Ala Ala His Gly Thr Pro Gly Pro
    290                 295                 300

Leu Ala Trp Asp Gly Gly Ala Gly Phe Thr Ser Glu Asp Gly Arg Gly
305                 310                 315                 320

Gly Ile Thr Leu Arg Val Ala Val Ala Asn Gly Leu Gly Asn Ala Lys
                325                 330                 335

Lys Leu Ile Thr Lys Met Gln Ala Gly Glu Ala Lys Tyr Asp Phe Val
            340                 345                 350

Glu Ile Met Ala Cys Pro Ala Gly Cys Val Gly Gly Gly Gly Gln Pro 355                 360                 365
Arg Ser Thr Asp Lys Ala Ile Thr Gln Lys Arg Gln Ala Ala Leu Tyr
    370                 375                 380

Asn Leu
385

<210> SEQ ID NO 6
<211> LENGTH: 441
<212> TYPE: PRT
<213> ORGANISM: Chlamydomonas reinhardtii

<400> SEQUENCE: 6

Ala Ala Pro Ala Ala Glu Ala Pro Leu Ser His Val Gln Gln Ala Leu
1               5                   10                  15

Ala Glu Leu Ala Lys Pro Lys Asp Asp Pro Thr Arg Lys His Val Cys
            20                  25                  30

Val Gln Val Ala Pro Ala Val Arg Val Ala Ile Ala Glu Thr Leu Gly
        35                  40                  45

Leu Ala Pro Gly Ala Thr Thr Pro Lys Gln Leu Ala Glu Gly Leu Arg
    50                  55                  60

Arg Leu Gly Phe Asp Glu Val Phe Asp Thr Leu Phe Gly Ala Asp Leu
65                  70                  75                  80

Thr Ile Met Glu Glu Gly Ser Glu Leu Leu His Arg Leu Thr Glu His
                85                  90                  95

Leu Glu Ala His Pro His Ser Asp Glu Pro Leu Pro Met Phe Thr Ser
            100                 105                 110

Cys Cys Pro Gly Trp Ile Ala Met Leu Glu Lys Ser Tyr Pro Asp Leu
        115                 120                 125

Ile Pro Tyr Val Ser Ser Cys Lys Ser Pro Gln Met Met Leu Ala Ala
    130                 135                 140

Met Val Lys Ser Tyr Leu Ala Glu Lys Gly Ile Ala Pro Lys Asp
145                 150                 155                 160

Met Val Met Val Ser Ile Met Pro Cys Thr Arg Lys Gln Ser Glu Ala
                165                 170                 175

Asp Arg Asp Trp Phe Cys Val Asp Ala Asp Pro Thr Leu Arg Gln Leu
            180                 185                 190

Asp His Val Ile Thr Thr Val Glu Leu Gly Asn Ile Phe Lys Glu Arg
        195                 200                 205

Gly Ile Asn Leu Ala Glu Leu Pro Glu Gly Glu Trp Asp Asn Pro Met
    210                 215                 220

Gly Val Gly Ser Gly Ala Gly Val Leu Phe Gly Thr Thr Gly Gly Val
225                 230                 235                 240

Met Glu Ala Ala Leu Arg Thr Ala Tyr Glu Leu Phe Thr Gly Thr Pro
                245                 250                 255

Leu Pro Arg Leu Ser Leu Ser Glu Val Arg Gly Met Asp Gly Ile Lys
            260                 265                 270

Glu Thr Asn Ile Thr Met Val Pro Ala Pro Gly Ser Lys Phe Glu Glu
        275                 280                 285

Leu Leu Lys His Arg Ala Ala Ala Arg Ala Glu Ala Ala His Gly
    290                 295                 300

Thr Pro Gly Pro Leu Ala Trp Asp Gly Ala Gly Phe Thr Ser Glu
305                 310                 315                 320

Asp Gly Arg Gly Gly Ile Thr Leu Arg Val Ala Val Ala Asn Gly Leu
                325                 330                 335

```
Gly Asn Ala Lys Lys Leu Ile Thr Lys Met Gln Ala Gly Glu Ala Lys
                340                 345                 350

Tyr Asp Phe Val Glu Ile Met Ala Cys Pro Ala Gly Cys Val Gly Gly
            355                 360                 365

Gly Gly Gln Pro Arg Ser Thr Asp Lys Ala Ile Thr Gln Lys Arg Gln
        370                 375                 380

Ala Ala Leu Tyr Asn Leu Asp Glu Lys Ser Thr Leu Arg Arg Ser His
385                 390                 395                 400

Glu Asn Pro Ser Ile Arg Glu Leu Tyr Asp Thr Tyr Leu Gly Glu Pro
                405                 410                 415

Leu Gly His Lys Ala His Glu Leu Leu His Thr His Tyr Val Ala Gly
            420                 425                 430

Gly Val Glu Glu Lys Asp Glu Lys Lys
        435                 440

<210> SEQ ID NO 7
<211> LENGTH: 379
<212> TYPE: PRT
<213> ORGANISM: Chlamydomonas reinhardtii

<400> SEQUENCE: 7

Cys Ile Ile Ala Cys Pro Val Ala Ala Leu Ser Glu Lys Ser His Met
1               5                   10                  15

Asp Arg Val Lys Asn Ala Leu Asn Ala Pro Glu Lys His Val Ile Val
                20                  25                  30

Ala Met Ala Pro Ser Val Arg Ala Ser Ile Gly Glu Leu Phe Asn Met
            35                  40                  45

Gly Phe Gly Val Asp Val Thr Gly Lys Ile Tyr Thr Ala Leu Arg Gln
        50                  55                  60

Leu Gly Phe Asp Lys Ile Phe Asp Ile Asn Phe Gly Ala Asp Met Thr
65                  70                  75                  80

Ile Met Glu Glu Ala Thr Glu Leu Val Gln Arg Ile Glu Asn Asn Gly
                85                  90                  95

Pro Phe Pro Met Phe Thr Ser Cys Cys Pro Gly Trp Val Arg Gln Ala
                100                 105                 110

Glu Asn Tyr Tyr Pro Glu Leu Leu Asn Asn Leu Ser Ser Ala Lys Ser
            115                 120                 125

Pro Gln Gln Ile Phe Gly Thr Ala Ser Lys Thr Tyr Tyr Pro Ser Ile
        130                 135                 140

Ser Gly Leu Asp Pro Lys Asn Val Phe Thr Val Thr Val Met Pro Cys
145                 150                 155                 160

Thr Ser Lys Lys Phe Glu Ala Asp Arg Pro Gln Met Glu Lys Asp Gly
                165                 170                 175

Leu Arg Asp Ile Asp Ala Val Ile Thr Thr Arg Glu Leu Ala Lys Met
            180                 185                 190

Ile Lys Asp Ala Lys Ile Pro Phe Ala Lys Leu Glu Asp Ser Glu Ala
        195                 200                 205

Asp Pro Ala Met Gly Glu Tyr Ser Gly Ala Gly Ala Ile Phe Gly Ala
    210                 215                 220

Thr Gly Gly Val Met Glu Ala Ala Leu Arg Ser Ala Lys Asp Phe Ala
225                 230                 235                 240

Glu Asn Ala Glu Leu Glu Asp Ile Glu Tyr Lys Gln Val Arg Gly Leu
                245                 250                 255

Asn Gly Ile Lys Glu Ala Glu Val Glu Ile Asn Asn Lys Tyr Asn
            260                 265                 270
```

-continued

```
Val Ala Val Ile Asn Gly Ala Ser Asn Leu Phe Lys Phe Met Lys Ser
        275                 280                 285

Gly Met Ile Asn Glu Lys Gln Tyr His Phe Ile Glu Val Met Ala Cys
        290                 295                 300

His Gly Gly Cys Val Asn Gly Gly Gly Gln Pro His Val Asn Pro Lys
305                 310                 315                 320

Asp Leu Glu Lys Val Asp Ile Lys Lys Val Arg Ala Ser Val Leu Tyr
                325                 330                 335

Asn Gln Asp Glu His Leu Ser Lys Arg Lys Ser His Glu Asn Thr Ala
            340                 345                 350

Leu Val Lys Met Tyr Gln Asn Tyr Phe Gly Lys Pro Gly Glu Gly Arg
        355                 360                 365

Ala His Glu Ile Leu His Phe Lys Tyr Lys Lys
        370                 375

<210> SEQ ID NO 8
<211> LENGTH: 31
<212> TYPE: DNA
<213> ORGANISM: Artificial Sequence
<220> FEATURE:
<223> OTHER INFORMATION: Other Information: Primer sequence

<400> SEQUENCE: 8
cacgctgttt ggcatcgacc tgaccatcat g                              31

<210> SEQ ID NO 9
<211> LENGTH: 31
<212> TYPE: DNA
<213> ORGANISM: Artificial Sequence
<220> FEATURE:
<223> OTHER INFORMATION: Other Information: Primer sequence

<400> SEQUENCE: 9
gccacggcca cgcggaatgt gatgccgccc c                              31
```